(12) United States Patent
Su et al.

(10) Patent No.: US 7,488,836 B2
(45) Date of Patent: Feb. 10, 2009

(54) COSTUNOLIDE DERIVATIVES

(75) Inventors: Weiguo Su, Shanghai (CN); Hong Jia, Shanghai (CN); Weihan Zhang, Shanghai (CN); Xiaoqiang Yan, Shanghai (CN); Jifeng Duan, Shanghai (CN); Tao Wang, Shanghai (CN); Yu Cai, Shanghai (CN)

(73) Assignee: Hutchison Medipharma Enterprises Limited, Nassau (BS)

( * ) Notice: Subject to any disclaimer, the term of this patent is extended or adjusted under 35 U.S.C. 154(b) by 0 days.

(21) Appl. No.: 11/838,503

(22) Filed: Aug. 14, 2007

(65) Prior Publication Data

US 2008/0051396 A1    Feb. 28, 2008

Related U.S. Application Data

(60) Provisional application No. 60/837,770, filed on Aug. 15, 2006.

(51) Int. Cl.
*C07D 307/00*    (2006.01)
(52) U.S. Cl. ..................................... 549/302
(58) Field of Classification Search ................ 549/302
See application file for complete search history.

(56) References Cited

U.S. PATENT DOCUMENTS

| 5,905,089 A | 5/1999 | Hwang et al. |
| 2005/0272716 A1 | 12/2005 | Crooks et al. |

OTHER PUBLICATIONS

Macias et al. Tetrahedron (2004), 60(38), 8477-8488.*
Choi et al. STN Accession No. 2002:935701, Document No. 138:378745, Abstract of Biological & Pharmaceutical Bulletin (2002), 25(11), 1446-1450.*
El-Feraly, STN Accession No. 1985:21216, Document No. 102:21216, Abstract of Phytochemistry (Elsevier) (1984), 23(10), 2372-4.*
Kang et al., "Costunolide Inhibits Interleukin-1β Expression by Down-Regulation of AP-1 and MAPK Activity in LPS-Simulated RAW 264.7 Cells," Biochemical and Biophysical Research Communication, 313:171-177 (2004).
*Synthesis of melampolides and cis,cis-germacranolides as natural herbicide models*; Francisco A. Macias, Raul F. Velasco, Jose A. Alvarex, Diego Castellano and Juan C.G. Galindo; 2004 Elsevier Ltd.; 8477-8488.

* cited by examiner

*Primary Examiner*—D. Margaret Seaman
*Assistant Examiner*—Nizal S Chandrakumar
(74) *Attorney, Agent, or Firm*—Occhiuti Rohlicek & Tsao LLP

(57) ABSTRACT

A compound of the following formula:

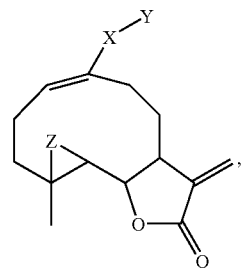

wherein X, Y, and Z are as defined herein. Also disclosed are methods for inhibiting TNFα expression, IL-1β expression, iNOS expression, and NF-κB activity and methods for treating autoimmune disease, cancer, or atherosclerosis with such a compound.

12 Claims, No Drawings

COSTUNOLIDE DERIVATIVES

CROSS-RELATED APPLICATIONS

This application claims the benefit of U.S. Provisional Application No. 60/837,770, filed on Aug. 15, 2006. The content of which is hereby incorporated by reference in its entirety.

BACKGROUND

Tumor necrosis factor alpha (TNFα), a mononuclear cytokine, possesses various biological activities, such as killing cancer cells or inhibiting growth of cancer cells, enhancing the phagocytosis of neutrophilic granulocyte, and up-regulating the production of peroxide region. Interleukin-1 beta (IL-1β), a cytokine secreted by monocyte macrophages and dendritic cells, mediates immune and inflammatory responses. Nuclear factor-kappa B (NF-κB), a pro-inflammatory transcription factor, upregulates cytokines (e.g., TNFα and IL-1β) and thereby mediates the inflammatory response. Inducible nitric oxide synthase (iNOS) is induced by endotoxins or cytokines (e.g., TNFα and IL-1β). It catalyzes the production of nitric oxide, an important pleiotropic molecule, from L-arginine and oxygen.

TNFα, IL-1β, NF-κB, and iNOS all play critical roles in important physiological and pathological processes. A wide range of diseases, e.g., autoimmune disease, cancer, atherosclerosis, or diabetes, can be treated by modulating their expression or activity. See, e.g., Ogata H, Hibi T. et al *Curr Pharm Des.* 2003; 9(14): 1107-13; Taylor P C. et al *Curr Pharm Des.* 2003; 9(14): 1095-106; Fan C., et al. *J. Mol. Med* 1999, 77, 577-592; and Alcaraz et al., *Current Pharmaceutical Design*, 2002: 8, 215.

SUMMARY

This invention is based on an unexpected finding that a number of costunolide derivatives inhibited effect on the expression of TNFα, IL-1β, and iNOS, and the activity of NF-κB.

One aspect of this invention features costunolide derivatives having the following formula:

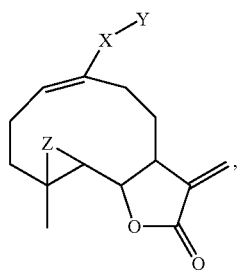

in which X is $CH_2$ and Y is $NR_1R_2$, $OCONR_1R_2$, $SR_1$, or $OR_3$; or X is C(O) and Y is $NR_1R_2$, $OR_1$, or $SR_1$; in which each of $R_1$ and $R_2$, independently, is H, alkyl, cycloalkyl, heterocycloalkyl, alkenyl, alkynyl, aryl, or heteroaryl, or $R_1$, $R_2$, and N to which they are attached, taken together, form a saturated or unsaturated 3-8 membered ring, optionally substituted with $R_1'$, $OR_2'$, $NR_2'R_3'$, $SR_2'$, $C(O)R_2'$, $CO_2R_2'$, or $C(O)NR_2'R_3'$, $R_1'$ being alkyl, cycloalkyl, heterocycloalkyl, heterocycloalkyl, alkenyl, alkynyl, aryl, or heteroaryl, and each of $R_2'$ and $R_3'$, independently, being H, alkyl, cycloalkyl, heterocycloalkyl, alkenyl, alkynyl, aryl, or heteroaryl; and $R_3$ is alkyl, cycloalkyl, heterocycloalkyl, alkenyl, alkynyl, aryl, or heteroaryl; and Z is a bond or O.

Referring to the compounds of the above formula, a subset features that Y is $NR_1R_2$, in which $R_1$ and $R_2$, independently, is H, alkyl, or aryl; or $NR_1R_2$, together, is a morpholinyl or piperidinyl. Another subset features that X is C(O) and Y is $OR_1$, in which $R_1$ is H or alkyl; or X is $CH_2$ and Y is $OR_3$, in which $R_3$ is alkyl. A further subset features Z is a double bond.

Shown below are exemplary compounds of this invention:

| No. | Name | Structure |
|---|---|---|
| 1 | (3aR,6Z,10E,11aR)-10-methyl-3-methylene-2-oxo-2,3,3a,4,5,8,9,11a-octahydrocyclodeca[b]furan-6-carboxylic acid | 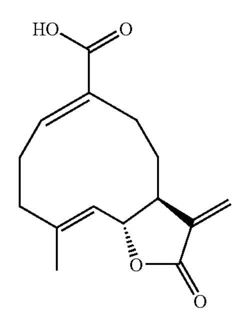 |

-continued

| No. | Name | Structure |
|---|---|---|
| 2 | (3aR,6Z,10E,11aR)-N,10-dimethyl-3-methylene-2-oxo-2,3,3a,4,5,8,9,11a-octahydrocyclodeca[b]furan-6-carboxamide | 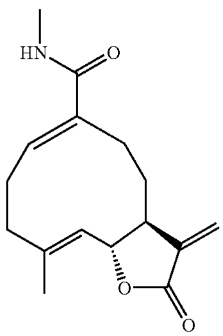 |
| 3 | (3aR,6Z,10E,11aR)-N,N-diethyl-10-methyl-3-methylene-2-oxo-2,3,3a,4,5,8,9,11a-octahydrocyclodeca[b]furan-6-carboxamide | 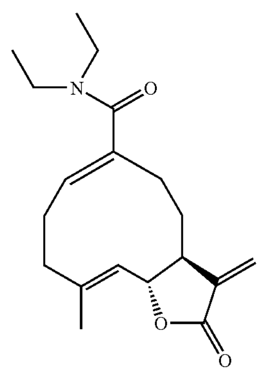 |
| 4 | (3aR,6Z,10E,11aR)-10-methyl-3-methylene-2-oxo-N-propyl-2,3,3a,4,5,8,9,11a-octahydrocyclodeca[b]furan-6-carboxamide | 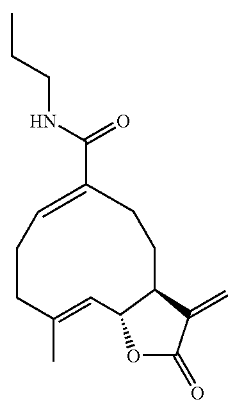 |
| 5 | (3aR,6Z,10E,11aR)-10-methyl-3-methylene-6-(piperidine-1-carbonyl)-3,3a,4,5,8,9-hexahydrocyclodeca[b]furan-2(11aH)-one | 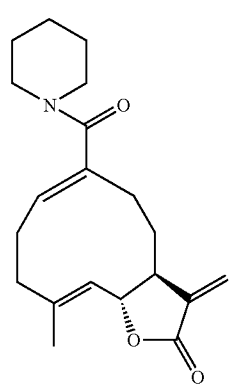 |

-continued

| No. | Name | Structure |
|---|---|---|
| 6 | (3aR,6Z,10E,11aR)-10-methyl-3-methylene-6-(morpholine-4-carbonyl)-3,3a,4,5,8,9-hexahydrocyclodeca[b]furan-2(11aH)-one | 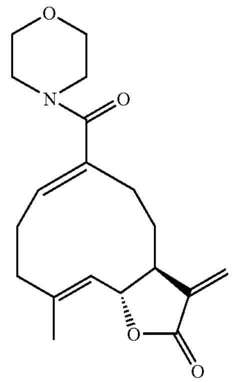 |
| 7 | (3aR,6Z,10E,11aR)-10-methyl-3-methylene-6-((propylamino)methyl)-3,3a,4,5,8,9-hexahydrocyclodeca[b]furan-2(11aH)-one | 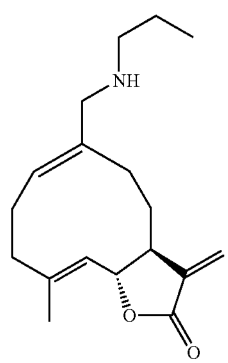 |
| 8 | (3aR,6Z,10E,11aR)-6-((2-hydroxyethylamino)methyl)-10-methyl-3-methylene-3,3a,4,5,8,9-hexahydrocyclodeca[b]furan-2(11aH)-one | 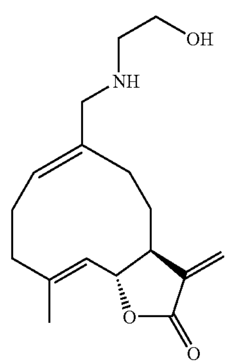 |
| 9 | (3aR,6Z,10E,11aR)-10-methyl-3-methylene-6-(morpholinomethyl)-3,3a,4,5,8,9-hexahydrocyclodeca[b]furan-2(11aH)-one | 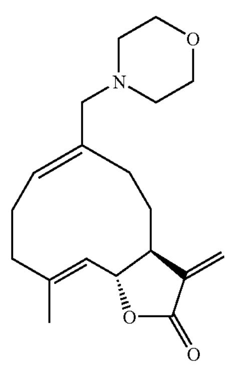 |

-continued

| No. | Name | Structure |
|---|---|---|
| 10 | (3aR,6Z,10E,11aR)-10-methyl-3-methylene-2-oxo-N-(4-fluoro-benzyl)-2,3,3a,4,5,8,9,11a-octahydrocyclodeca[b]furan-6-carboxamide | 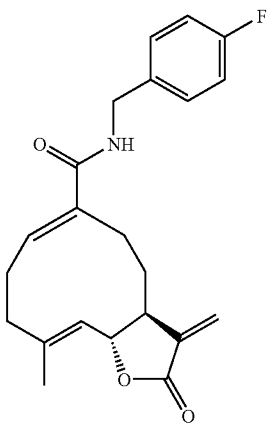 |
| 11 | (3aR,6Z,10E,11aR)-10-methyl-3-methylene-2-oxo-N-(4-phenoxyphenyl)-2,3,3a,4,5,8,9,11a-octahydrocyclodeca[b]furan-6-carboxamide | 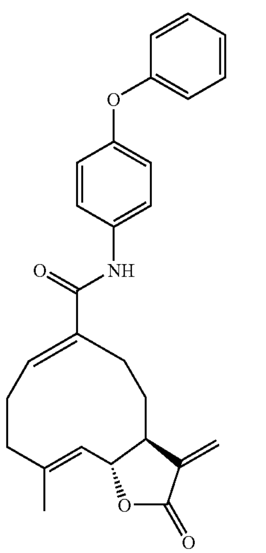 |
| 12 | (3aR,6Z,10E,11aR)-10-methyl-3-methylene-2-oxo-N-(2-methoxyethyl)-2,3,3a,4,5,8,9,11a-octahydrocyclodeca[b]furan-6-carboxamide | 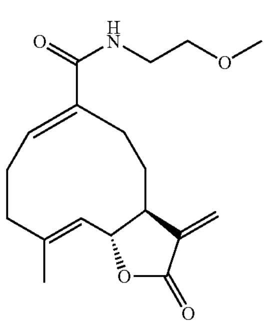 |

| No. | Name | Structure |
|---|---|---|
| 13 | (3aR,6Z,10E,11aR)-10-methyl-3-methylene-2-oxo-N-(3-(N-methylbenzamide)-2,3,3a,4,5,8,9,11a-octahydrocyclodeca[b]furan-6-carboxamide | 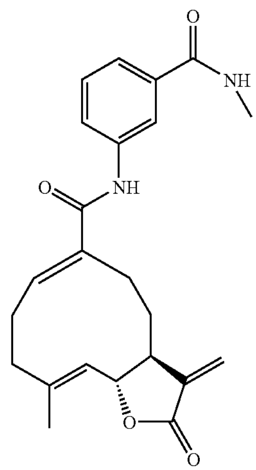 |
| 14 | (3aR,6Z,10E,11aR)-methyl-10-methyl-3-methylene-2-oxo-2,3,3a,4,5,8,9,11a-octahydrocyclodeca[b]furan-6-carboxylate | 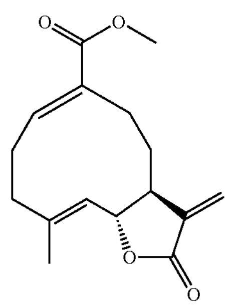 |
| 15 | ((3aR,6Z,10E,11aR)-10-methyl-3-methylene-2-oxo-2,3,3a,4,5,8,9,11a-octahydrocyclodeca[b]furan-6-yl)methyl cyclopropylcarbamate | 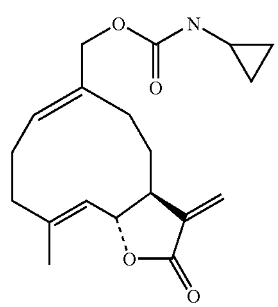 |
| 16 | ((3aR,6Z,10E,11aR)-10-methyl-3-methylene-2-oxo-2,3,3a,4,5,8,9,11a-octahydrocyclodeca[b]furan-6-yl)methyl benzylcarbamate | 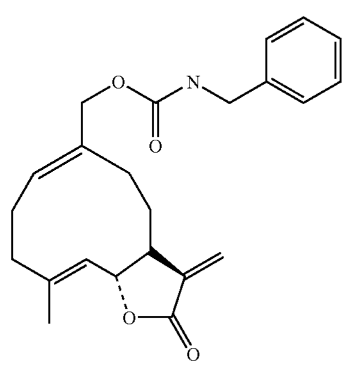 |

-continued

| No. | Name | Structure |
|---|---|---|
| 17 | ((3aR,6Z,10E,11aR)-10-methyl-3-methylene-2-oxo-2,3,3a,4,5,8,9,11a-octahydrocyclodeca[b]furan-6-yl)methyl ethylcarbamate | 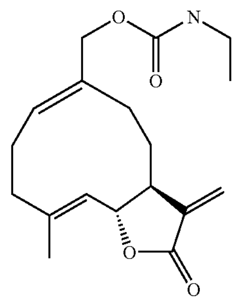 |

The term "alkyl," unless stated otherwise, refers to a straight or branched hydrocarbon containing 1-20 carbon atoms. Examples of alkyl groups include, but are not limited to, methyl, ethyl, n-propyl, i-propyl, n-butyl, i-butyl, and t-butyl.

The term "alkenyl" refers to a straight or branched hydrocarbon having one or more carbon-carbon double bonds. The term "alkynyl" refers to a straight or branched hydrocarbon having one or more carbon-carbon triple bonds. Alkenyl and alkynyl, unless stated otherwise, contain 1-20 carbon atoms.

The term "cycloalkyl," unless stated otherwise, refers to a saturated and partially unsaturated cyclic hydrocarbon group having 3 to 12 carbon atoms. Examples of cyclyl groups include, but are not limited to, cyclopropyl, cyclobutyl, cyclopentyl, cyclopentenyl, cyclohexyl, cyclohexenyl, cycloheptyl, and cyclooctyl. The term "heterocycloalkyl" refers to a saturated or partially unsaturated cyclic hydrocarbon group having 2 to 12 carbon atoms and at least one heteroatom selected from N, O, and S.

The term "aryl," unless stated otherwise, refers to a 6-carbon monocyclic, 10-carbon bicyclic, 14-carbon tricyclic aromatic ring system wherein each ring may have 1 to 4 substituents. Examples of aryl groups include, but are not limited to, phenyl, naphthyl, and anthracenyl.

The term "heteroaryl" refers to an aromatic 5-8 membered monocyclic, 8-12 membered bicyclic, or 11-14 membered tricyclic ring system having one or more heteroatoms (such as O, N, or S). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, aryl, heteroaryl can be either substituted or unsubstituted. For examples, these moieties can be substituted with groups containing zero to six heteroatoms selected from halogen, oxygen, sulfur, and nitrogen. Possible substituents on alkenyl, alkynyl, cycloalkyl, heterocycloalkyl, aryl, and heteroaryl include alkyl, alkenyl, alkynyl, cycloalkyl, heterocycloalkyl, alkoxy, aryl, aryloxy, heteroaryl, heteroaryloxy, amino, alkylamino, dialkylamino, arylamino, diarylamino, hydroxyl, halogen, thio, alkylthio, arylthio, alkylsulfonyl, arylsulfonyl, acylamino, aminoacyl, amidino, guanidino, ureido, cyano, nitro, acyl, acyloxy, carboxyl, and carboxylic ester. Possible substituents on alkyl include all of the above-said substituents except alkyl.

The compounds described above include their pharmaceutically acceptable salts and prodrugs, if applicable. Such a salt can be formed between a positively charged ionic group in the compounds (e.g., ammonium) and a negatively charged counterion (e.g., trifluoroacetate). Likewise, a negatively charged ionic group in the compounds (e.g., carboxylate) can also form a salt with a positively charged counterion (e.g., sodium, potassium, calcium, or magnesium). The compounds may contain a non-aromatic double bond and one or more asymmetric centers. Thus, they can occur as racemic mixtures, single enantiomers, individual diastereomers, diastereomeric mixtures, and cis- or trans-isomeric forms. All such isomeric forms are contemplated. As an example, the compounds of this invention can be isomers having the stereochemistry as shown in the following formula:

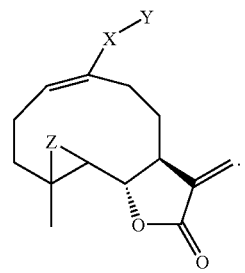

Another aspect of this invention features a method of inhibiting the expression of TNFα, IL-1β, or iNOS, or inhibiting the activity of NF-κB. More specifically, the method includes administering to a subject in need thereof an effective amount of the compound of the following formula:

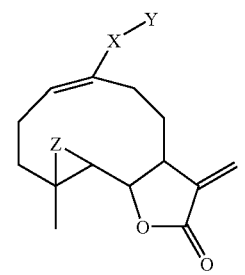

In which X is $CH_2$ or C(O); Y is $NR_1R_2$, $OCONR_1R_2$, $OR_1$, or $SR_1$; in which each of $R_1$ and $R_2$, independently, is H, alkyl, cycloalkyl, heterocycloalkyl, alkenyl, alkynyl, aryl, or heteroaryl, or $R_1$, $R_2$, and N to which they are attached, taken together, form a saturated or unsaturated 3-8 membered ring, optionally substituted with $R_1'$, $OR_2'$, $NR_2'R_3'$, $SR_2'$, $C(O)R_2'$, $CO_2R_2'$, $C(O)NR_2'R_3'$, $R_1'$ being alkyl, cycloalkyl, heterocycloalkyl, alkenyl, alkynyl, aryl, or heteroaryl, and each of $R_2'$ and $R_3'$, independently, being H, alkyl, cycloalkyl, heterocycloalkyl, alkenyl, alkynyl, aryl, or heteroaryl; and Z is a bond or O; or a pharmaceutically acceptably salt or a stereoisomer thereof.

Still another aspect of this invention features a method of treating disease associated with TNFα, IL-1β, iNOS, or NF-κB (e.g., autoimmune disease, cancer, atherosclerosis, or diabetes) by administering to a subject in need thereof an effective amount of one or more the just-described compounds.

Also within the scope of this invention is a composition containing the above-described compound and a pharmaceutically acceptable carrier for use in treating autoimmune disease, cancer, atherosclerosis, or diabetes, as well as the use of such a composition for the manufacture of a medicament for treating such a disease.

The details of one or more embodiments of the invention are set forth in the description below. Other features, objects, and advantages of the invention will be apparent from the description and from the claims.

DETAILED DESCRIPTION

The compounds of this invention can be synthesized by synthetic methods well known in the art. An exemplary synthetic route is shown in Scheme 1 below.

In Scheme 1, the starting costunolide aldehyde and chloro derivatives of costunolide can be prepared by the method described in Macias F. A., et al. *Tetra. Lett.*, 2004, 60, 8477-8488. They are transformed to an amino compound by reductive amination or an ether (thioether) compound by substitution.

As another example, carboxy, amide, or ester derivatives of costunolide can be prepared from costunolide aldehyde. As shown in Scheme 2 below, the aldehyde compound can be readily oxidized to give a carboxylic acid. The carboxylic acid is reacted with an amino compound to form an amide compound.

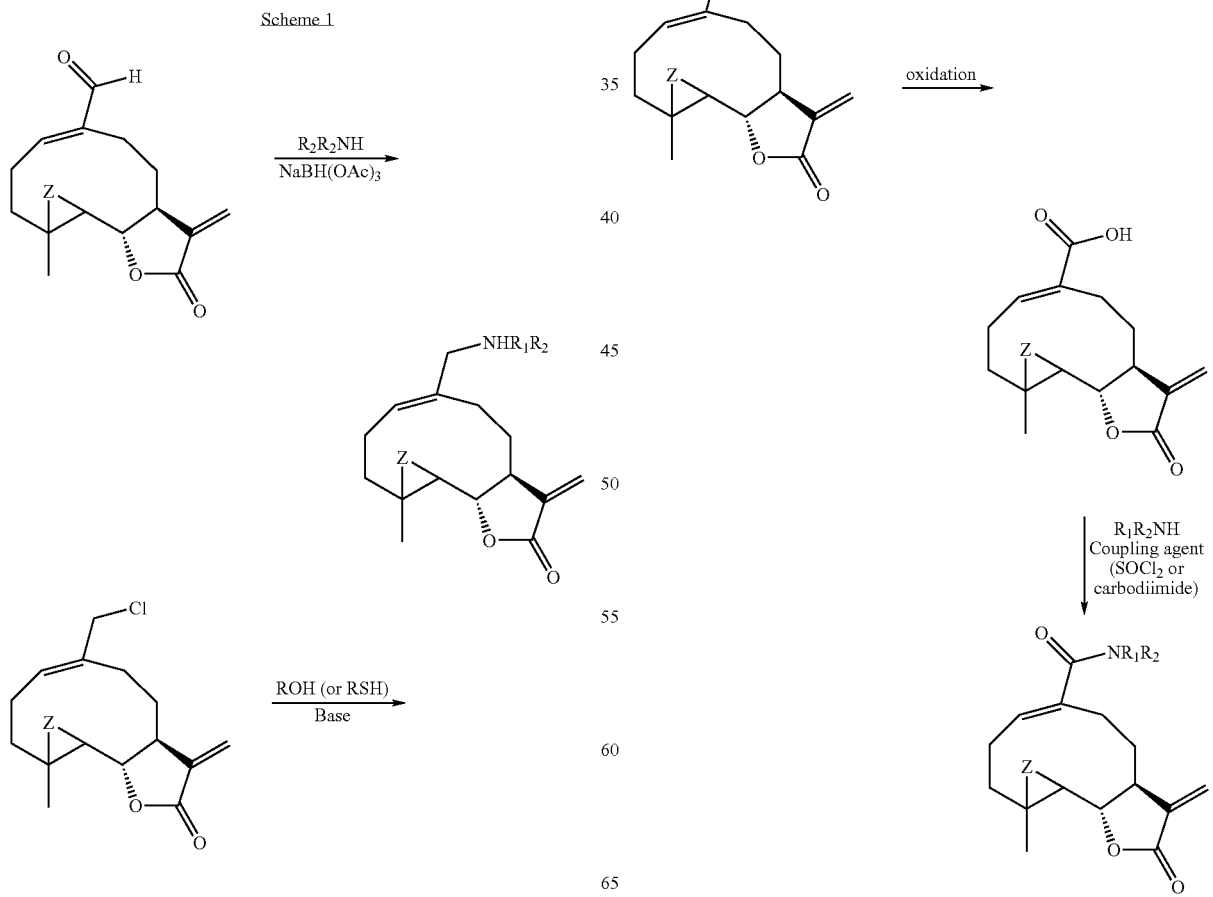

Scheme 3 below illustrates an example of synthesizing costunolide carbamate compounds from costunolide alcohol. Costunolide alcohol can be prepared by the method described in Macias F. A., et al. *Tetra. Lett.*, 2004, 60, 8477-8488.

Scheme 3:

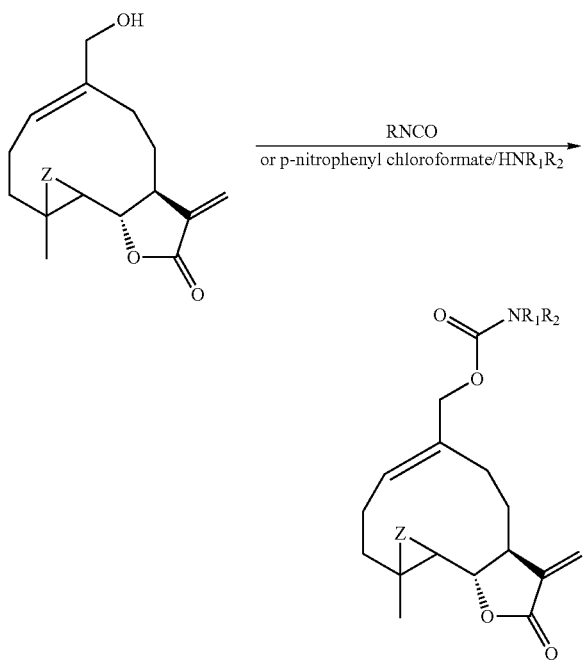

The above-described synthetic methods demonstrate the synthesis of only certain costunolide derivatives of this invention. A skilled person in the art, in view of these examples, would be able to modify the methods to synthesize other costunolide derivatives of this invention. Alternatively, the skilled person can use other methods well known in the art to synthesize the costunolide derivatives of this invention. The compounds thus synthesized can be further purified by column chromatography, high performance liquid chromatography, or crystallization.

Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The costunolide derivatives described above show effective inhibition against expression of TNFα, IL-1β, and iNOS and activity of NF-κB. Thus, this invention relates to a method of inhibiting expression of TNFα, IL-1β, and iNOS and activity of NF-κB by contacting it with an effective amount of one or more costunolide derivatives. Also included in this invention is a method of treating autoimmune disease, cancer, atherosclerosis by administering to a subject who needs the treatment an effective amount of one or more of the costunolide derivatives described above. Examples of the autoimmune disease includes, but are not limited to, rheumatoid arthritis, osteoarthritis, inflammatory bowels diseases, psoriasis, multiple sclerosis, sepsis, or diabetes. The term "treating" refers to application or administration of one or more of the costunolide derivatives to a subject, who has autoimmune disease, cancer, or atherosclerosis, a symptom of the disease, or a predisposition toward the disease, with the purpose to cure, heal, alleviate, relieve, alter, remedy, ameliorate, improve, or affect the disease, the symptom, or the predisposition. "An effective amount" refers to the amount of the costunolide derivative which is required to confer the desired effect on the subject. Effective amounts vary, as recognized by those skilled in the art, depending on route of administration, excipient usage, and the possibility of co-usage with other therapeutic treatments such as use of other active agents.

To practice the methods of this invention, a composition having one or more of the costunolide derivatives described above can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol and water. In addition, fixed oils are conventionally employed as a solvent or suspending medium (e.g., synthetic mono- or diglycerides). Fatty acids, such as oleic acid and its glyceride derivatives, are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having an active costunolide derivative can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active costunolide derivative. Examples of other carriers include colloidal silicon oxide, magnesium stearate, cellulose, sodium lauryl sulfate, and D&C Yellow #10.

The costunolide derivatives of this invention can be preliminarily screened by an in vitro assay for one or more of their desired activities, e.g., inhibiting expression of TNFα, IL-1β, or iNOS, or activity of NF-κB. Compounds that demonstrate high activities in the preliminary screening can further be screened for their efficacy by in vivo assays. For example, a test compound can administered to an animal model (e.g., a mouse having autoimmune disease, cancer, or atherosclerosis) and its therapeutic effect is then accessed. Based on the results, an appropriate dosage range and administration route can also be determined.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All of the publications cited herein are hereby incorporated by reference in their entirety.

EXAMPLE 1

Synthesis of (3aR,6Z,10E,11aR)-10-methyl-3-methylene-2-oxo-2,3,3a,4,5,8,9,11a-octahydrocyclodeca[b]furan-6-carboxylic acid To a solution of costunolide aldehyde (1 mmol) in t-BuOH (30 mL) and 2-methyl-2-butene (7 mL) was added a buffer solution of $NaClO_2$ (10 mmol) and $NaH_2PO_4$ (7.4 mmol) in 9 mL of $H_2O$. The reaction mixture was stirred at room temperature for 2 hours. After removal of the solvent in vacuo and addition of $H_2O$, the mixture was extracted with EtOAc. The organic layers were combined, washed with a saturated sodium chloride solution, dried with anhydrous sodium sulfate, and concentrated in vacuo.

$^1$H NMR ($CDCl_3$, 300 MHz): 6.862 (t, J=9.0 Hz,1H), 6.180 (d, J=3.3 Hz,1H), 5.458 (d, J=3.3 Hz,1H), 5.118 (t, J=10.2 Hz,1H),4.627 (t, J=9.6 Hz,1H), 2.813-2.690 (m,1H), 2.420-2.044 (m,8H), 1.275(s,3H);

MS: 263.0(M+1).

EXAMPLE 2

Synthesis of (3aR,6Z,10E,11aR)-N,10-dimethyl-3-methylene-2-oxo-2,3,3a,4,5,8,9,11a-octahydrocyclodeca[b]furan-6-carboxamide To a solution of the acid product of Example 1 (0.1 mmol) in $CH_2Cl_2$ (5 mL) was added $C_2O_2Cl_2$ (0.12 mmol) and DMF (in a catalytic amount). The reaction mixture was stirred for 2 hours. The solvent was removed in vacuo.

The resultant residue was dissolved in $CH_2Cl_2$ (2 mL) and was added dropwise to a mixture of methylamine hydrochloride (0.1 mmol) and pyridine (0.1 mmol) in $CH_2Cl_2$ (5 mL) and stirred for another 30 mins. $H_2O$ was added and the mixture was extracted with EtOAc. The organic layers were combined, washed with a saturated sodium chloride solution, dried with anhydrous sodium sulfate, and concentrated in vacuo to provide the desired product at the yield of 70%.

$^1$H NMR ($CDCl_3$, 300 MHz): 6.137 (t, J=3.3 Hz, 1H), 5.962 (t, J=7.2 Hz,1H), 5.440 (d, J=3.3 Hz, 1H), 5.094 (d, J=10.5 Hz, 1H), 4.605 (t, J=9.0 Hz,1H), 2.849 (d, J=5.1 Hz, 3H), 2.586-2.412 (m, 3H), 2.281-2.187 (m, 2H), 2.088-1.894 (m, 3H), and 1.854 (s, 3H);

MS: 276.3 (M+1).

EXAMPLE 3

Synthesis of (3aR,6Z,10E,11aR)-N,N-diethyl-10-methyl-3-methylene-2-oxo-2,3,3a,4,5,8,9,11a-octahydrocyclodeca[b]furan-6-carboxamide The compound was prepared at the yield of 65% following the procedure described in Example 2 except that diethylamine (0.1 mmol) was used in place of methylamine hydrochloride.

$^1$H NMR ($CDCl_3$, 300 MHz): 6.131 (t, J=3.3 Hz, 1H), 5.542 (t, J=7.2 Hz, 1H), 5.342 (d, J=3.3 Hz, 1H), 5.266 (d, J=9.6 Hz, 1H), 4.621 (t, J=9.6 Hz, 1H), 3.389 (br, 4H), 3.177-3.102 (m, 1H), 2.328-1.979 (m, 8H), 3.035-2.973 (m, 1H), 1.594 (s, 3H), 1.165 (t, J=7.2 Hz, 6H);

MS: 318.3 (M+1).

EXAMPLE 4

Synthesis of (3aR,6Z,10E,11aR)-10-methyl-3-methylene-2-oxo-N-propyl-2,3,3a,4,5,8,9,11a-octahydrocyclodeca[b]furan-6-carboxamide The compound was prepared following the procedure described in Example 2 except that propylamine (0.1 mmol) was used in place of methylamine hydrochloride. The yield is 65%.

$^1$H NMR ($CDCl_3$, 300 MHz): 6.158 (d, J=3.3 Hz, 1H), 5.955 (t, J=7.2 Hz, 1H), 5.439 (d, J=2.7 Hz, 1H), 5.088 (d, J=10.2 Hz, 1H), 4.625 (t, J=10.2 Hz, 1H), 3.304-3.228 (m, 3H),2.579-2.455 (m, 3H), 2.300-2.202 (m, 2H), 1.917-1.868 (m, 3H),1.590-1.495 (m, 5H), 0.934 (t, J=7.2 Hz, 3H);

MS: 304.4 (M+1).

EXAMPLE 5

Synthesis of (3aR,6Z,10E,11aR)-10-methyl-3-methylene-6-(piperidine-1-carbonyl)-3,3a,4,5,8,9-hexahydrocyclodeca[b]furan-2(11aH)-one The compound was prepared following the procedure described in Example 2 except that piperidine (0.1 mmol) was used in place of methylamine hydrochloride. The yield is 55%.

$^1$H NMR ($CDCl_3$, 300 MHz): 6.144(d, J=3.3 Hz, 1H), 5.586 (t, J=7.2 Hz, 1H), 5.384 (d, J=3.3 Hz, 1H), 5.244 (d, J=10.5 Hz, 1H), 5.628 (t, J=10.2 Hz, 1H), 3.517 (m, 4H), 2.999 (m, 1H), 2.260-1.869 (m, 8H), 1.660-1.504 (m, 10H);

MS: 330.3 (M+1).

EXAMPLE 6

Synthesis of (3aR,6Z,10E,11aR)-10-methyl-3-methylene-6-(morpholine-4-carbonyl)-3,3a,4,5,8,9-hexahydrocyclodeca[b]furan-2(11aH)-one The compound was prepared following the procedure described in Example 2 except that morpholine (0.1 mmol) was used in place of methylamine hydrochloride. The yield is 58%.

$^1$H NMR ($CDCl_3$, 300 MHz): 6.159 (d, J=3.6 Hz,1H), 5.591 (t, J=8.7 Hz,1H), 5.393 (d, J=3.3 Hz, 1 H), 4.629 (d, J=10.2 Hz, 1H), 4.629 (t, J=10.2 Hz, 1H), 3.644-3.522 (m, 8H), 2.986 (br, 1H), 2.273-1.917 (m, 8H), 1.610 (s, 3H);

MS: 332.3(M+1).

EXAMPLE 7

Synthesis of (3aR,6Z,10E,11aR)-10-methyl-3-methylene-6-((propylamino)methyl)-3,3a,4,5,8,9-hexahydrocyclodeca[b]furan-2(11aH)-one To a solution of costunolide aldehyde (0.1 mmol) and propylamine (0.1 mmol) in CH$_2$Cl$_2$ (2 mL) was added NaHCO$_3$ (0.5 mmol). The mixture was stirred at room temperature for 3 hours. NaB(O$_2$CCH$_3$)$_3$H (1 mmol) was added. The resultant mixture was stirred overnight, filtered, and evaporated under reduced pressure. The residue was purified by chromatography column using CH$_2$Cl$_2$/CH$_3$OH to produce the title compound at the yield of 50%.

$^1$H NMR (CDCl$_3$, 300 MHz): 6.166 (d, J=3.6 Hz, 1H), 5.428 (d, J=3.3 Hz, 1H), 5.402 (t, J=8.4 Hz, 1H), 5.072 (d, J=10.2 Hz, 1H), 4.616 (d, J=9.6 Hz, 1H), 3.254 (d, J=13.2 Hz, 1H), 3.089(d, J=13.2 Hz, 1H), 2.556-2.480 (m, 4H),2.388-2.286(m,1H), 2.181-1.899 (m,6H), 1.550-1.453 (m, 2H), 1.245 (s, 3H), 0.926 (t, J=7.2 Hz,3H);

MS: 290.3 (M+1).

EXAMPLE 8

Synthesis of (3aR,6Z,10E,11aR)-6-((2-hydroxyethylamino)methyl)-10-methyl-3-methylene-3,3a,4,5,8,9-hexahydrocyclodeca[b]furan-2(11aH)-one The compound was prepared following the procedure described in Example 7 except that hydroxyethylamine (0.1 mmol) was used in place of propylamine. The yield is 60%.

$^1$H NMR (CDCl$_3$, 300 MHz): 6.179 (d, J=2.4 Hz, 1H), 5.450-5.400 (m, 2H), 5.063 (d, J=10.2 Hz, 1H), 4.624 (d, J=9.6 Hz, 1H), 3.663 (br, 2H), 3.309 (d, J=13.5 Hz, 1H), 3.096 (d, J=13.5 Hz, 1H), 2.909-2.738 (m, 6H), 2.197-1.908 (m, 5H), 0.871 (s, 3H);

MS: 292.2 (M+1).

EXAMPLE 9

Synthesis of (3aR,6Z,10E,11aR)-10-methyl-3-methylene-6-(morpholinomethyl)-3,3a,4,5,8,9-hexahydrocyclodeca[b]furan-2(11aH)-one The compound was prepared following the procedure described in Example 7 except that morpholine (0.1 mmol) was used in place of propylamine. The yield is 50%.

$^1$H NMR (CDCl$_3$, 300 MHz): 6.181 (d, J=3.6 Hz, 1H), 5.424 (d, J=3.0 Hz, 1H), 5.365 (t, J=7.8 Hz, 1H), 5.059 (d, J=9.9 Hz, 1H), 4.632 (d, J=9.9 Hz, 1H), 3.680-3.650 (m, 4H), 3.095 (d, J=11.7 Hz, 1H), 2.617 (d, J=12.6 Hz, 1H),2.392-1.851 (m, 9H), 1.251 (s, 3H);

MS: 318.2 (M+1).

EXAMPLE 10

Synthesis of (3aR,6Z,10E,11aR)-10-methyl-3-methylene-2-oxo-N-(4-fluoro-benzyl)-2,3,3a,4,5,8,9,11a-octahydrocyclodeca[b]furan-6-carboxamide The compound was prepared following the procedure described in Example 2 except that 4-fluorobenzylamine (0.1 mmol) was used in place of methylamine hydrochloride. The yield is 80%.

$^1$H NMR (CDCl$_3$, 300 MHz): 7.246-7.201 (t, J=8.4 Hz, 2H), 7.018-6.961 (t, J=8.4 Hz, 2H), 6.175 (d, J=3.0 Hz, 1H), 6.030 (t, J=7.5 Hz, 1H), 5.406 (d, J=2.7 Hz, 1H), 5.076 (d, J=10.5 Hz, 1H), 4.625 (t, J=9.3 Hz,1H), 4.470 (d, J=4.8 Hz, 2H), 2.980-2.426 (m, 3H), 2.288-1.876 (m, 6H), 1.876 (s, 3H);

MS: 368.1 (M−1).

EXAMPLE 11

Synthesis of (3aR,6Z,10E,11aR)-10-methyl-3-methylene-2-oxo-N-(4-phenoxyphenyl)-2,3,3a,4,5,8,9,11a-octahydrocyclodeca[b]furan-6-carboxamide The compound was prepared following the procedure described in Example 2 except that 4-phenoxyphenylamine (0.1 mmol) was used in place of methylamine hydrochloride. The yield is 80%.

$^1$H NMR (CDCl$_3$, 300 MHz): 7.682 (s, 1H), 7.522 (d, J=7.2 Hz, 2H), 7.354 (d, J=7.5 Hz, 2H), 7.300 (d, J=8.1 Hz, 2H), 7.118 (t, J=7.5 Hz, 1H), 7.005 (d, J=7.5 Hz, 2H), 6.197 (t, J=7.5 Hz, 1H), 6.132 (d, J=3.3 Hz, 1H), 5.435 (d, J=3.3 Hz, 1H), 5.198 (d, J=10.2 Hz, 1H), 4.652 (t, J=9.0 Hz, 1H), 2.650-2.568 (m,3H), 2.326-2.294 (m,3H), 2.089-2.041 (m, 3H), 1.902(s, 3H);

MS: 430.5 (M−1).

EXAMPLE 12

Synthesis of (3aR,6Z,10E,11aR)-10-methyl-3-methylene-2-oxo-N-(2-methoxyethyl)-2,3,3a,4,5,8,9,11a-octahydrocyclodeca[b]furan-6-carboxamide The compound was prepared following the procedure described in Example 2 except that 2-methoxyethylamine (0.1 mmol) was used in place of methylamine hydrochloride. The yield is 70%.

$^1$H NMR (CDCl$_3$, 300 MHz): 6.090 (d, J=3.6 Hz, 1H), 5.950 (t, J=7.5 Hz, 1H), 5.373 (d, J=3.3 Hz, 1H), 5.043 (t, J=10.2 Hz, 1H), 4.533(t, J=10.2 Hz, 1H), 3.397-3.373 (m, 4H), 3.261 (s, 3H), 2.478-2.406 (m,3H), 2.216-2.144 (m,2H), 2.003-1.894 (m, 4H), 1.894(s,3H);

MS: 320.4 (M+1).

EXAMPLE 13

Synthesis of (3aR,6Z,10E,11aR)-10-methyl-3-methylene-2-oxo-N-(3-(N-methylbenzamide)-2,3,3a,4,5,8,9,11a-octahydrocyclodeca[b]furan-6-carboxamide The compound was prepared following the procedure described in Example 2 except that 3-amino-N-methylbenzamide (0.1 mmol) was used in place of methylamine hydrochloride. The yield is 75%.

$^1$H NMR (CDCl$_3$, 300 MHz): 7.859 (s, 1H), 7.698 (br, 1H), 7.396 (d, J=7.2 Hz, 1H), 7.209-7.205 (m, 1H), 6.165 (m, 1H), 6.077 (d, J=3.3 Hz, 1H), 5.320 (d, J=3.3 Hz, 1H), 5.185 (d, J=6.9 Hz, 1H), 4.536 (t, J=9.9 Hz, 1H), 2.960 (s, 3H), 2.484-1.956 (m, 9H), 1.815 (s, 3H).

MS: 395.5 (M+1).

EXAMPLE 14

Synthesis of methyl (3aR,6Z,10E,11aR)-10-methyl-3-methylene-2-oxo-2,3,3a,4,5,8,9,11a-octahydrocyclodeca[b]furan-6-carboxylate Concentrated sulfuric acid (2 mL) was added slowly to a solution of the acid product of Example 1 (0.1 mmol) in 20 mL absolute methanol. The mixture was refluxed overnight, cooled to room temperature, and diluted with brine. The resultant solution was extracted with 3×20 mL CHCl$_3$. The combined organic layers were washed with a saturated sodium bicarbonate solution and brine, dried over magnesium sulfate, and concentrated in vacuo. The residue was purified by column chromatography to provide the desired product in a yield of 82%.

$^1$H NMR(CDCl$_3$, 300 MHz): 6.714 (t, J=7.8 Hz, 1H), 6.176 (d, J=3.0 Hz, 1H), 5.458 (d,J=3.0 Hz, 1H), 5.117 (d, J=10.2 Hz, 1H), 4.625 (t, J=9.9 Hz, 1H), 3.747 (s, 3H), 2.760-2.638 (m, 1H), 2.483-2.025 (m, 8H), 1.879 (s, 3H);

MS: 277.4 (M+1).

EXAMPLE 15

Synthesis of ((3aR,6Z,10E,11aR)-10-methyl-3-methylene-2-oxo-2,3,3a,4,5,8,9,11a-octahydrocyclodeca[b]furan-6-yl)methyl cyclopropylcarbamate To costunolide alcohol (0.1 mmol) in 5 mL anhydrous methylene chloride were added p-nitrophenyl chloroformate (0.1 mmol) and triethylamine (0.1 mmol). The reaction mixture was stirred at room temperature for 2 hours. After addition of cyclopropylamine (0.1 mmol), the mixture was stirred overnight and then diluted with water (5 mL). It was extracted three times with methylene chloride. The combined organic layers were washed with saturated brine and dried over anhydrous sodium sulfate. After concentration in vacuo, the residue was purified by column chromatography to provide the desired product in a yield of 38%.

$^1$H NMR(CDCl$_3$, 300 MHz): 6.178 (d, J=3.6 Hz, 1H), 5.560-5.512 (m, 1H), 5.447 (d, J=3.2 Hz, 1H), 5.076 (d, J=6.4 Hz,1 Hz), 4.839 (br,1H), 4.612-4.587 (t, J=10.0 Hz, 2H), 4.456 (br,1H), 2.578-1.843 (m, 12H), 1.571 (m,1H), 0.724 (br, 2H), 0.504 (br, 2H);

MS: 332.2 (M+1).

EXAMPLE 16

Synthesis of ((3aR,6Z,10E,11aR)-10-methyl-3-methylene-2-oxo-2,3,3a,4,5,8,9,11a-octahydrocyclodeca[b]furan-6-yl)methyl benzylcarbamate To costunolide alcohol (0.1 mmol) in 5 mL methylene chloride were added benzyl isocyanate (0.1 mmol), 4-N,N'dimethylamino pyridine (0.1 mmol) and triethylamine (0.1 mmol). The mixture was stirred overnight, diluted with 5 mL water, and extracted three times with methylene chloride. The combined organic layers were washed with saturated brine and dried over anhydrous sodium sulfate. After concentration in vacuo, the residue was purified by column chromatography to provide the desired product in a yield of 70%.

$^1$H NMR (CDCl$_3$, 400 MHz): 7.347-7.253 (m,5H), 6.153 (d, J=3.6 Hz, 1H), 5.557 (t, J=7.2 Hz, 1H), 5.411 (d, J=2.0 Hz, 1H), 5.070 (m, 2H), 4.643 (d, J=12.0,1H), 4.611 (t, J=7.5 Hz, 1H), 4.499 (d, J=12.0 Hz, 1H), 4.364 (d, J=6.0 Hz, 1H), 2.621-2.571 (m, 1H), 2.194-1.840 (m, 11H);

MS: 382.3 (M+1).

EXAMPLE 17

Synthesis of ((3aR,6Z,10E,11aR)-10-methyl-3-methylene-2-oxo-2,3,3a,4,5,8,9,11a-octahydrocyclodeca[b]furan-6-yl)methylethylcarbamate The compound was prepared following the procedure described in Example 16 except that ethyl isocyanate was used in place of benzyl isocyanate. The yield is 39%.

$^1$H NMR(CDCl$_3$, 400 MHz): 6.154 (d, J=3.2 Hz, 1H), 5.531 (t, J=7.6 Hz, 1H), 5.424 (d, J=3.6 Hz, 1H), 5.057 (d, J=10.0 Hz, 1H), 4.590 (m, 2H), 4.433(d, J=12.4 Hz, 1H), 3.203-3.170(m, 2H), 2.604-2.542(m, 1H), 2.360-2.296(m, 1H), 2.148-1.821(m, 10H), 1.118(t, J=7.2 Hz, 3H);

MS: 319.9 (M+1).

EXAMPLE 18

Inhibition of NF-κB Activity

An in vitro assay was conducted to evaluate the efficacy of the above-obtained compounds in inhibiting TNFα-induced NF-κB activation in 293 HEK cells.

Human Embryonic Kidney (HEK) 293 cells were purchased from American Tissue Culture Collection (Manassas, Va.) and cultured in DMEM media containing 10% FBS at 37° C. with 5% CO$_2$. The cells were cotransfected with pNFκB-luc and pcDNA3.1. Stably transfected pNFKB-luc-293 clones were selected in the presence of 0.6 mg/ml G418. These cells were seeded in a 96-well plate at 3×10$^4$ cells/well.

A series of dilute DMEM solutions were prepared for each of the above-synthesized compounds and were subsequently added to wells containing the selected HEK 293 cells. The final concentrations of the compound in the wells were 0.1, 0.3, 1, 3, and 10 μM. After incubated for 15 minutes, the cells were stimulated with 10 ng/ml recombinant human TNFα for 4 hours. Wells containing 0.1 μg/mL Triptolide and 10 ng/ml recombinant human TNFα were used as positive control. Cells containing 10 μl DMEM media and 10 ng/ml recombinant human TNFα were used as negative control. Cells containing 10 μl DMEM media, not TNFα and the tested compounds were used as the background.

The treated cells were lysed, and luciferase activity was measured with the Luciferase Assay System (Promega, WI, USA) using a Perkin-Elmer Victor 3 plate reader.

Inhibition Ratio (%)=[1−(drug treatment−background)/(negative control−background)]×100%

The results show that compounds 1-17 all inhibited TNFα-induced NF-κB activation.

EXAMPLE 19

Inhibition of TNFα, IL-1β, and iNOS Expression

In vitro assays were conducted to evaluate the efficacy of the above-obtained compounds in inhibiting expression of TNFα, IL-1β, and iNOS.

THP-1 cells (human monocytic cell line) and RAW 264.7 cells (Mouse leukaemic monocyte macrophage cell line) were purchased from American Tissue Culture Collection. The cells were cultured in RPMI 1640 or DMEM media containing 10% FBS at 5×10$^3$ cells/well).

A series of dilute DMEM solutions were prepared for each of the above-synthesized compounds and subsequently added to the wells. The final concentrations of the compound in the wells were 0.1, 0.3, 1, 3, and 10 μM. Wells containing 10 μM dexamethason were used as positive control. Wells containing 10 μl media were used as background. The plate was incubated at 37° C. under 5% CO$_2$ for 15 minutes. For cytokines induction, 10 μl of 10 μg/ml LPS was added to each well except for the wells having background and the cells were placed in a 37° C., 5% CO$_2$ incubator for 1 hour. For iNOS mRNA induction, 10 μl of 10 μg/ml LPS and 200 ng/mL mIFN-γ were added to each well except for the background wells and the cells were placed in a 37° C., 5% CO$_2$ incubator for 8 hours. Finally, THP-1 cells were treated with a lysis buffer containing TNFα or IL-1β target probes at 53° C. for 0.5 hour and RAW264.7 cells were treated with a lysis buffer containing iNOS target probes at 53° C. for 0.5 hour.

The lysate of cells were analyzed using bDNA assay kits (QuantiGene™, GenoSpectra, US) according to the manufacturer's protocol. The oligonucleotide probes derived from human TNFα (GenBank NM_000594), human IL-1β (GenBank NM_000576), and mouse inducible nitric oxide synthase 2 (iNOS, GenBank NM_010927) were synthesized by Invitrogen Biotechnology Company (Shanghai, China). Briefly, 100 μl of the cell lysate from each well was transferred to a well of a capture plate and incubated at 53° C. for 16 to 20 hours. After washing the capture plate with washing buffer, 100 μl of an Amplifier Working Reagent was added to each well and the plate was incubated at 53° C. for 1 hour. Following a wash, 100 μl of a Label Working Reagent was added to each well before being incubated at 53° C. for 1 hour. Finally, after washing the plate, 100 μl of a Substrate Working Reagent was added to each well. After incubation at 46° C. for 0.5 hour, the luminescence of each well was measured using a Perkin-Elmer Victor 3 plate reader.

Inhibition Ratio (%)=[1−(compound treatment−background)/(stimuli treatments−background)]×100%

The results show that compounds 1-17 all inhibited the mRNA expression of TNFα, IL-1β, and iNOS. Some compounds exhibited $IC_{50}$ values as low as 0.1 μM.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the costunolide derivatives of this invention can be made and used to practice this invention. Thus, other embodiments are also within the claims.

What is claimed is:
1. A compound of Formula (I):

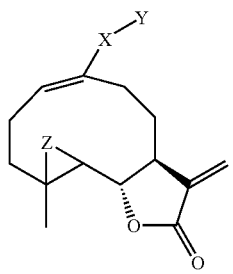

Formula (I)

wherein:
X is $CH_2$ and Y is $NR_1R_2$, $OCONR_1R_2$; or X is C(O) and Y is $NR_1R_2$; in which $R_1$ is alkyl, cycloalkyl, alkenyl, alkynyl, aryl, or heteroaryl; $R_2$ is H, alkyl, cycloalkyl, heterocycloalkyl, alkenyl, alkynyl, aryl, or heteroaryl, or $R_1$, $R_2$, and N to which they are attached, taken together, form a saturated or unsaturated 3-8 membered ring, optionally substituted with $R_1'$, $OR_2'$, $NR_2'R_3'$, $SR_2'$, $C(O)R_2'$, $CO_2R_2'$, or $C(O)NR_2'R_3'$, $R_1'$ being alkyl, cycloalkyl, heterocycloalkyl, alkenyl, alkynyl, aryl, or heteroaryl, and each of $R_2'$ and $R_3'$, independently, being H, alkyl, cycloalkyl, heterocycloalkyl, alkenyl, alkynyl, aryl, or heteroaryl; and Z is a bond;
or a pharmaceutically acceptably salt thereof.

2. The compound of claim 1, wherein Y is $NR_1R_2$ or $OCONR_1R_2$.

3. The compound of claim 2, wherein each of $R_1$ is alkyl or aryl and $R_2$ is H, alkyl, or aryl.

4. The compound of claim 2, wherein $NR_1R_2$, together, is a morpholinyl or piperidinyl.

5. The compound of claim 1, wherein X is C(O) and Y is $OR_1$, in which $R_1$ is H or alkyl.

6. The compound of claim 1, wherein X is $CH_2$ and Y is $OR_3$, in which $R_3$ is alkyl.

7. The compound of claim 1, wherein X is $CH_2$.

8. The compound of claim 1, wherein X is C(O).

9. The compound of claim 1, wherein Y is $NR_1R_2$ or $OCONR_1R_2$.

10. The compound of claim 9, wherein each of $R_1$ is alkyl or aryl and $R_2$ is H, alkyl, or aryl.

11. The compound of claim 9, wherein $NR_1R_2$, together, is a morpholinyl or piperidinyl.

12. The compound of claim 1, where in the compound is:

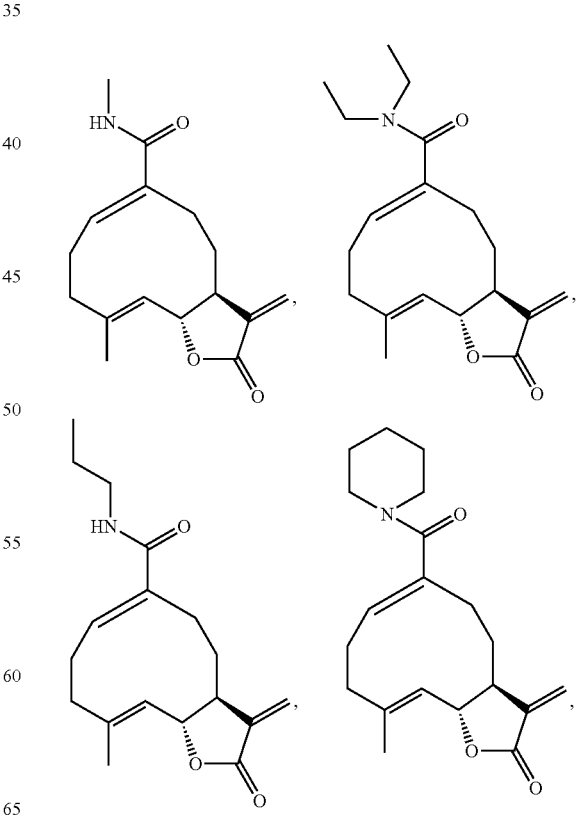

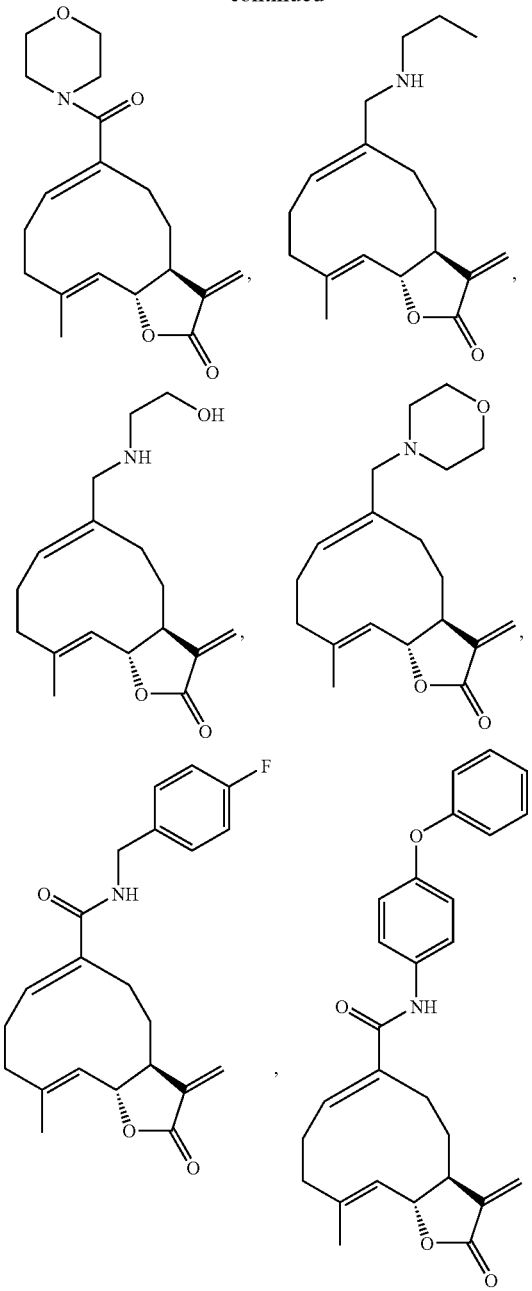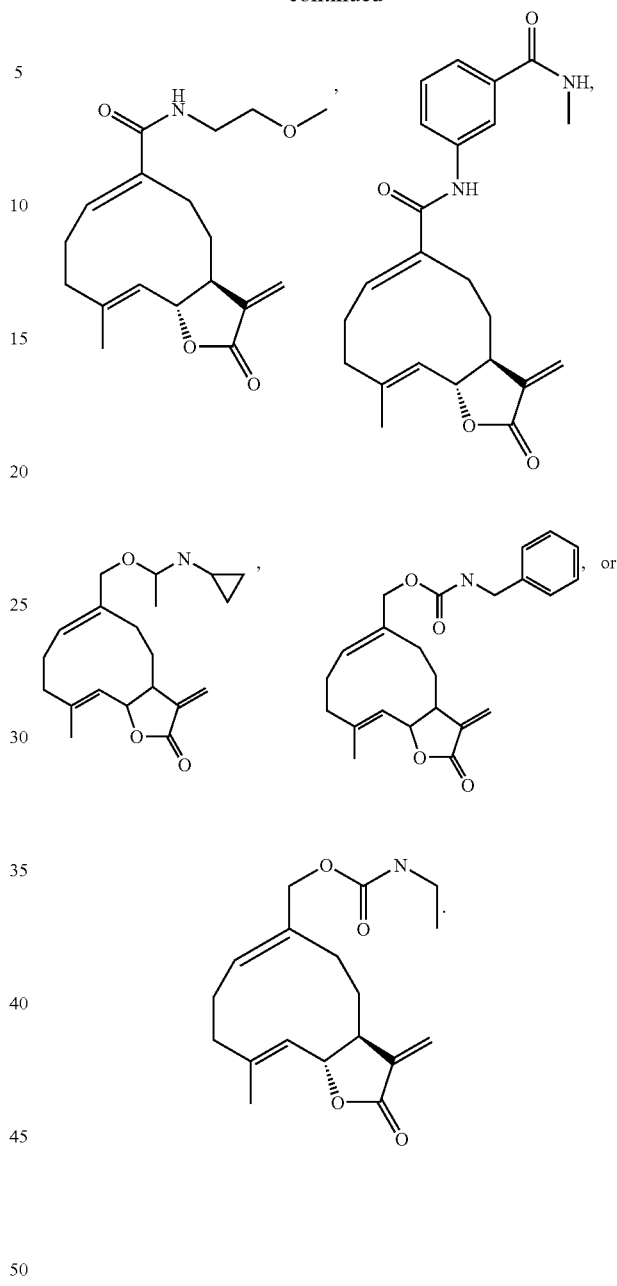

UNITED STATES PATENT AND TRADEMARK OFFICE
CERTIFICATE OF CORRECTION

PATENT NO.        : 7,488,836 B2
APPLICATION NO. : 11/838503
DATED             : February 10, 2009
INVENTOR(S)       : Su et al.

It is certified that error appears in the above-identified patent and that said Letters Patent is hereby corrected as shown below:

Col. 24, line 33, should read:
Claim 12. The compound of claim 1, where in the compound is:

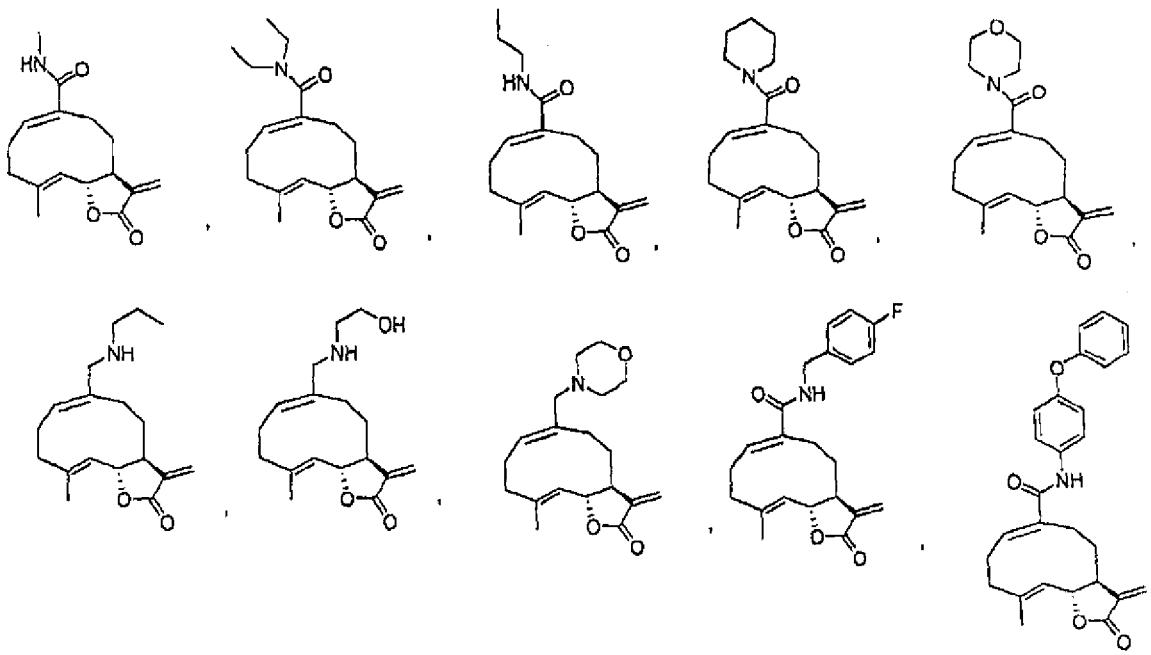

UNITED STATES PATENT AND TRADEMARK OFFICE
CERTIFICATE OF CORRECTION

PATENT NO. : 7,488,836 B2
APPLICATION NO. : 11/838503
DATED : February 10, 2009
INVENTOR(S) : Su et al.

It is certified that error appears in the above-identified patent and that said Letters Patent is hereby corrected as shown below:

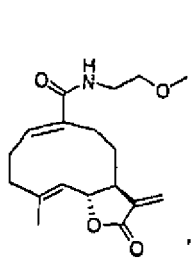 , 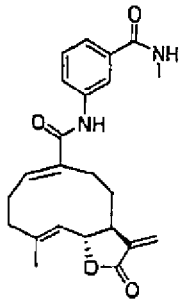 , 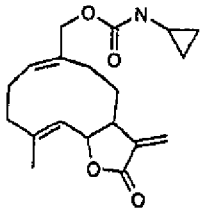 , 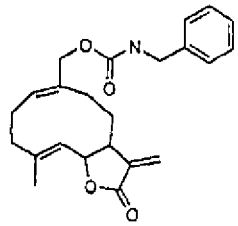 , or

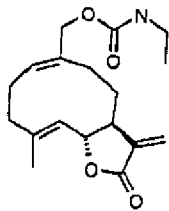 .

Signed and Sealed this

Twenty-sixth Day of May, 2009

JOHN DOLL
*Acting Director of the United States Patent and Trademark Office*